US012635936B2

(12) United States Patent
Chuang et al.

(10) Patent No.: US 12,635,936 B2
(45) Date of Patent: May 26, 2026

(54) DETECTING METHOD FOR BEHAVIOR DISORDER EVENT DURING RAPID EYE MOVEMENT SLEEP AND DETECTING SYSTEM THEREOF

(71) Applicant: ASUSTEK COMPUTER INC., Taipei (TW)

(72) Inventors: Pei-Chi Chuang, Taipei (TW); Chun-Hsiang Tsai, Taipei (TW); Yu-Jen Chen, Taipei (TW); Ching-Fu Wang, Taipei (TW); Shih-Zhang Li, Taipei (TW); Sheng-Huang Lin, Taipei (TW); Pei-Hsin Kuo, Taipei (TW); You-Yin Chen, Taipei (TW)

(73) Assignee: ASUSTEK COMPUTER INC., Taipei (TW)

( * ) Notice: Subject to any disclaimer, the term of this patent is extended or adjusted under 35 U.S.C. 154(b) by 656 days.

(21) Appl. No.: 17/977,183

(22) Filed: Oct. 31, 2022

(65) Prior Publication Data

US 2023/0337971 A1 Oct. 26, 2023

(30) Foreign Application Priority Data

Apr. 22, 2022 (TW) .................................. 111115438

(51) Int. Cl.
*A61B 5/00* (2006.01)
*A61B 5/0205* (2006.01)
*A61B 5/352* (2021.01)

(52) U.S. Cl.
CPC .......... *A61B 5/4812* (2013.01); *A61B 5/0205* (2013.01); *A61B 5/352* (2021.01); *A61B 5/7289* (2013.01)

(58) Field of Classification Search
CPC ..... A61B 5/7289; A61B 5/0205; A61B 5/352; A61B 5/4812
See application file for complete search history.

(56) References Cited

U.S. PATENT DOCUMENTS

2007/0293731 A1* 12/2007 Downs ................... G16H 40/67
600/300
2010/0100004 A1* 4/2010 Van Someren ...... A61B 5/4818
600/595

(Continued)

FOREIGN PATENT DOCUMENTS

CN 108992040 A 12/2018
CN 105902257 B 6/2019

(Continued)

OTHER PUBLICATIONS

Cole et al. "Automatic Sleep/Wake Identification from Wrist Actigraphy" published in Sleep, vol. 15, pp. 461-469 (1992) (Year: 1992).*

(Continued)

*Primary Examiner* — Amanda L Steinberg
(74) *Attorney, Agent, or Firm* — MUNCY, GEISSLER, OLDS & LOWE, P.C.

(57) ABSTRACT

A detecting method for a behavior disorder event during rapid-eye-movement sleep is provided. The detecting method includes: collecting a heart rate value and a motion value of a user per epoch within a time period; generating a plurality of corresponding sleep condition values by using the motion values, to distinguish epochs into an awake period and a sleep period; transforming the motion values corresponding to the sleep period into a score according to a predetermined rule, to generate a plurality of sleep depth scores, and distinguishing the sleep period into a light sleep period and a deep sleep period by using the sleep depth scores; grouping the heart rate values corresponding to the deep sleep period as a high heart rate group and a low heart rate group; and determining, when the motion values corresponding to the high heart rate group satisfy a condition, that a behavior disorder event happens.

12 Claims, 4 Drawing Sheets

Collect a heart rate value and a motion value of a user per epoch within a time period ~S110

Generate a plurality of corresponding sleep condition values by using the motion values, and distinguish the epochs into at least one awake period and at least one sleep period within the time period according to the sleep condition values, where each of the sleep condition values corresponds to at least two consecutive motion values ~S130

Transform each of the motion values corresponding to the at least one sleep period into a score according to a predetermined rule ~S150

Generate a plurality of sleep depth scores by using the scores, and distinguish the at least one sleep period into at least one light sleep period and at least one deep sleep period by using the sleep depth scores ~S160

Group the heart rate values corresponding to the at least one deep sleep period as a high heart rate group and a low heart rate group by using an unsupervised learning algorithm ~S170

Determine, when the motion values corresponding to the high heart rate group satisfy a condition, that a behavior disorder event during rapid eye movement sleep happens ~S190

(56) References Cited

U.S. PATENT DOCUMENTS

| | | | | |
|---|---|---|---|---|
| 2017/0055898 | A1* | 3/2017 | Bandyopadhyay | A61B 5/303 |
| 2020/0397365 | A1* | 12/2020 | Zhang | G16H 50/20 |
| 2021/0386300 | A1* | 12/2021 | Rogers | A61B 5/746 |
| 2022/0240843 | A1* | 8/2022 | Kokoszka | G16H 50/70 |
| 2023/0240595 | A1* | 8/2023 | Tiron | G16H 10/60 |
| | | | | 600/301 |

FOREIGN PATENT DOCUMENTS

| | | | |
|---|---|---|---|
| CN | 109222950 | B | 8/2021 |
| CN | 113784667 | A | 12/2021 |
| TW | 201742596 | A | 12/2017 |

OTHER PUBLICATIONS

"The complete guide to clustering analysis: k-means and hierarchical clustering by hand and in R" Antoine Soetewey, Feb. 13, 2020 (Year: 2020).*

Yi-Feng Ko et al; "Quantification Analysis of Sleep Based on Smartwatch Sensors for Parkinson's Disease," Biosensors, Jan. 27, 2022, pp. 1-18.

* cited by examiner

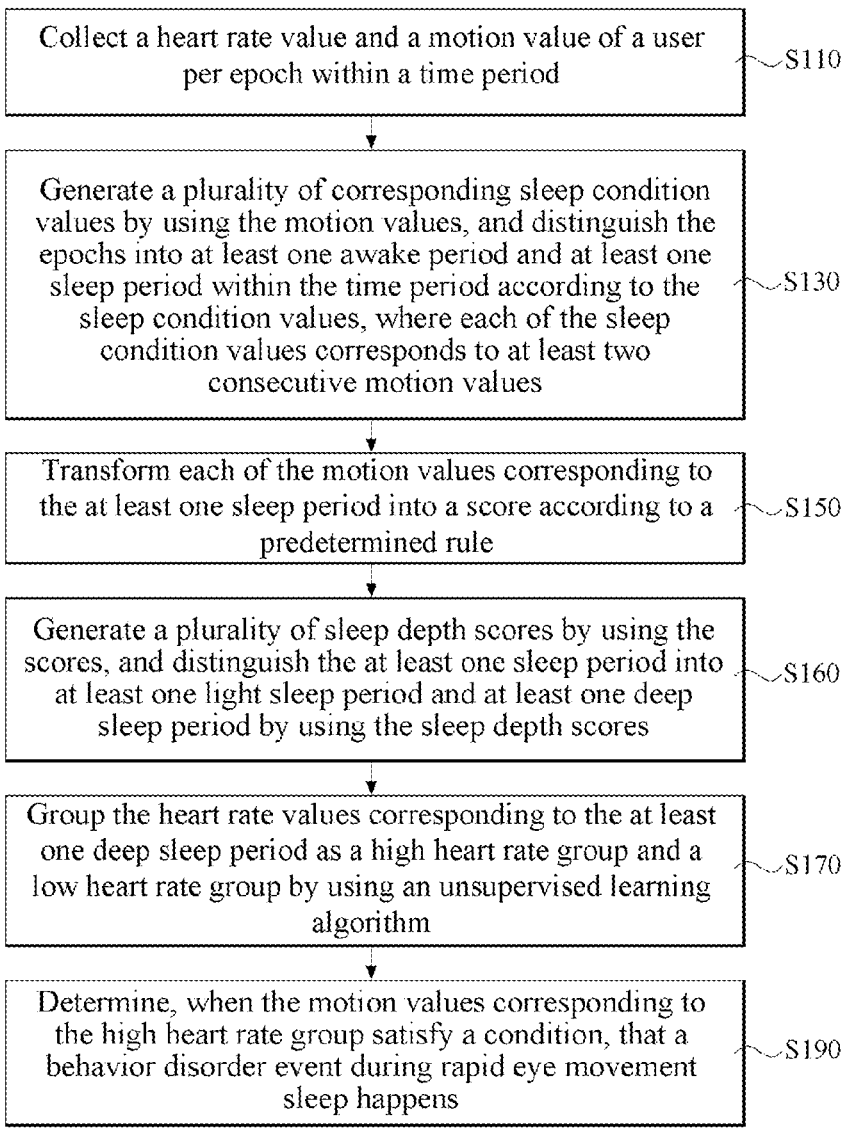

Collect a heart rate value and a motion value of a user per epoch within a time period ~S110

Generate a plurality of corresponding sleep condition values by using the motion values, and distinguish the epochs into at least one awake period and at least one sleep period within the time period according to the sleep condition values, where each of the sleep condition values corresponds to at least two consecutive motion values ~S130

Transform each of the motion values corresponding to the at least one sleep period into a score according to a predetermined rule ~S150

Generate a plurality of sleep depth scores by using the scores, and distinguish the at least one sleep period into at least one light sleep period and at least one deep sleep period by using the sleep depth scores ~S160

Group the heart rate values corresponding to the at least one deep sleep period as a high heart rate group and a low heart rate group by using an unsupervised learning algorithm ~S170

Determine, when the motion values corresponding to the high heart rate group satisfy a condition, that a behavior disorder event during rapid eye movement sleep happens ~S190

FIG. 1

DETECTING METHOD FOR BEHAVIOR DISORDER EVENT DURING RAPID EYE MOVEMENT SLEEP AND DETECTING SYSTEM THEREOF

CROSS-REFERENCE TO RELATED APPLICATION

This application claims the priority benefit of Taiwan Application Serial No. 111115438, filed on Apr. 22, 2022. The entirety of the above-mentioned patent application is hereby incorporated by reference herein and made a part of the specification.

BACKGROUND OF THE INVENTION

Field of the Invention

The disclosure relates to the field of sleep detection technologies, and in particular, to a detecting method for a behavior disorder event during rapid eye movement sleep and a detecting system thereof.

Description of the Related Art

A behavior disorder event during rapid eye movement sleep is closely related to an occurrence risk of cerebral neurological diseases.

The conventional detecting method for a behavior disorder event during rapid eye movement sleep needs to detect an event by using a polysomnography (PSG), in combination with an inertial measurement unit (IMU) or a light sensor, and then through interpretation by professional medical personnel. The detection process of the method is complex, and requires the professional medical personnel to participate in the interpretation. As a result, the detection process is difficult to implement, and is inapplicable to daily detection of patients or those at the risk of suffering from cerebral neurological diseases.

BRIEF SUMMARY OF THE INVENTION

The disclosure provides a detecting method for a behavior disorder event during rapid eye movement sleep, including: collecting a heart rate value and a motion value of a user per epoch within a time period; generating a plurality of corresponding sleep condition values by using the motion values, and distinguishing the epochs into at least one awake period and at least one sleep period within the time period according to the sleep condition values, where each of the sleep condition values is generated by using at least two consecutive motion values; transforming each of the motion values corresponding to the at least one sleep period into a score according to a predetermined rule, generating a plurality of sleep depth scores by using the scores, and distinguishing the at least one sleep period into at least one light sleep period and at least one deep sleep period by using the sleep depth scores; grouping the heart rate values corresponding to the at least one deep sleep period as a high heart rate group and a low heart rate group by using an unsupervised learning algorithm; and determining, when the motion values corresponding to the high heart rate group satisfy a condition, that a behavior disorder event during rapid eye movement sleep happens.

The disclosure further provides a detecting system for a behavior disorder event during rapid eye movement sleep. The detecting system includes an inertial measurement unit, a heart rate sensor, a memory, and a control unit. The control unit is electrically connected to the inertial measurement unit and the heart rate sensor. A heart rate value and a motion value of a user per epoch within a time period are collected through the inertial measurement unit and the heart rate sensor, and are stored in the memory. The control unit is configured to: generate a plurality of corresponding sleep condition values by using the motion values, and distinguish the epochs into at least one awake period and at least one sleep period within the time period according to the sleep condition values, where each of the sleep condition values is generated by using at least two consecutive motion values; transform each of the motion values corresponding to the at least one sleep period into a score according to a predetermined rule, generate a plurality of sleep depth scores by using the scores, and distinguish the at least one sleep period into at least one light sleep period and at least one deep sleep period by using the sleep depth scores; group the heart rate values corresponding to the at least one deep sleep period as a high heart rate group and a low heart rate group by using an unsupervised learning algorithm; and determine, when the motion values corresponding to the high heart rate group satisfy a condition, that a behavior disorder event during rapid eye movement sleep happens.

The disclosure provides a simple and convenient detecting method and detecting system, to quickly determine whether a behavior disorder event during rapid eye movement sleep happens to a user. The detecting method and detecting system are used matching a wearable electronic device, to effectively collect heart rate data and motion data of the user, thereby overcoming the conventional difficulty in detecting the behavior disorder event during rapid eye movement sleep.

BRIEF DESCRIPTION OF THE DRAWINGS

FIG. 1 shows an embodiment of a detecting method for a behavior disorder event during rapid eye movement sleep according to an embodiment of the disclosure;

DETAILED DESCRIPTION OF THE EMBODIMENTS

Figure 2:
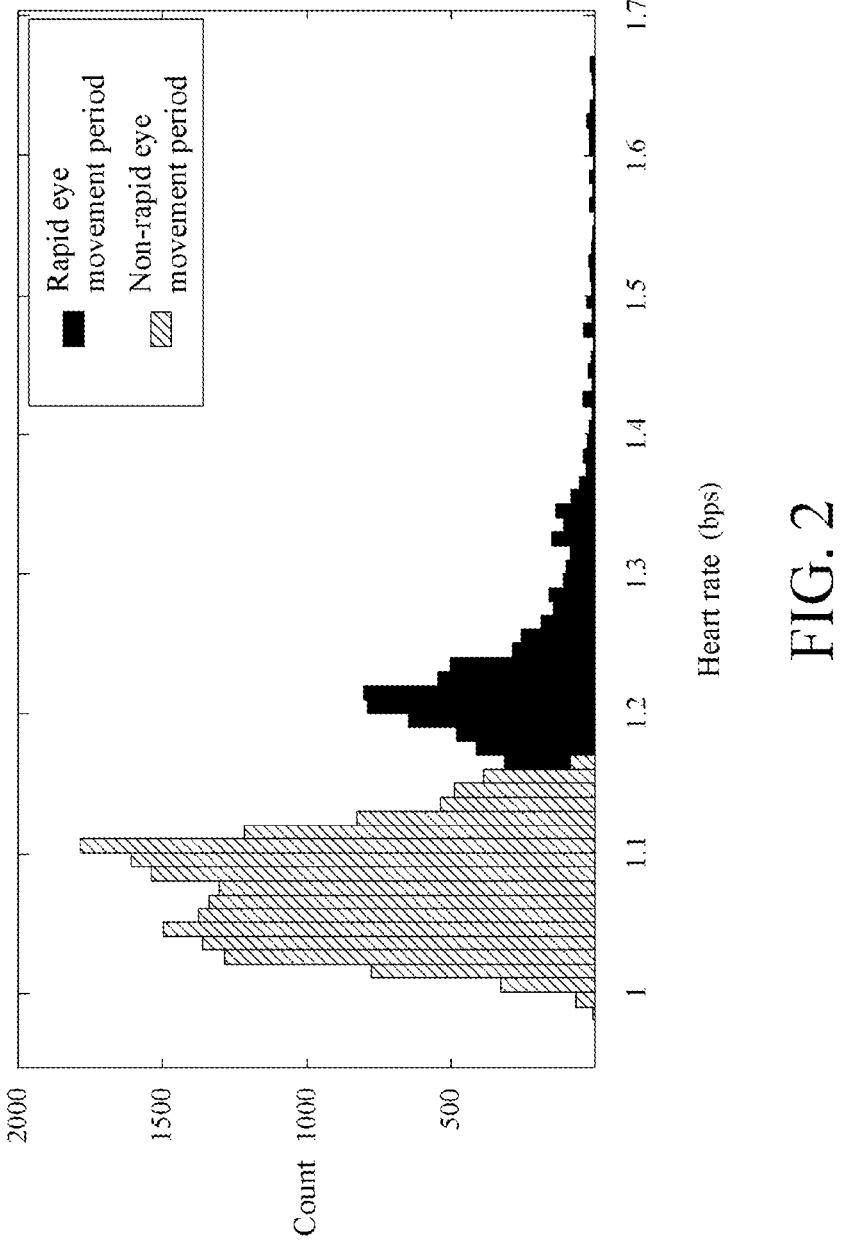
FIG. 2 is a bar chart showing an embodiment of a result of grouping heart rate values by using a K-means clustering algorithm.

More detailed descriptions of the specific embodiments of the disclosure are provided below with reference to the accompanying drawings. The features and advantages of the disclosure are described more clearly according to the following description and claims. All of the drawings use very simplified forms and imprecise proportions, only being used for assisting in conveniently and clearly explaining the objective of the embodiments of the disclosure.

FIG. 1 shows an embodiment of a detecting method for a behavior disorder event during rapid eye movement sleep according to an embodiment of the disclosure. As shown in the figure, the detecting method includes the following steps.

First, as described in step S110, a heart rate value and a motion value of a user per epoch within a time period are collected. In each epoch, only a piece of heart rate data and a piece of motion data are collected as the heart rate value and the motion value, or a plurality of pieces of heart rate data and a plurality of pieces of motion data are collected and then statistical calculation (in an embodiment, taking an average) is performed to obtain the heart rate value and the motion value.

In step S110, a wearable electronic device such as a smart watch or a smart band, is used to collect a heart rate value and a motion value of a user within a time period. In an embodiment, the epoch is 30 seconds, and the motion value is an inertial measurement value. In an embodiment, the inertial measurement value includes an X-direction acceleration measurement value, a Y-direction acceleration measurement value, and a Z-direction acceleration measurement value. The heart rate value is an R-wave-to-R-wave interval (RR interval) value of a photoplethysmogram (PPG) signal.

Then, as described in step S130, a plurality of corresponding sleep condition values is generated by using the motion values, and the epochs are distinguished into at least one awake period and at least one sleep period within the time period according to the sleep condition values, where each of the sleep condition values is generated by using at least two consecutive motion values.

In an embodiment, in step S130, the motion value of each epoch and the motion value of at least one adjacent epoch are used to calculate a sleep condition value corresponding to each epoch. Then, according to the sleep condition values, it is determined whether each epoch belongs to the awake period or the sleep period, and then the epochs are distinguished into at least one awake period and at least one sleep period within the time period.

In an embodiment, a Cole-Kripke algorithm is used to distinguish the epochs into the awake period and the sleep period within the time period. The Cole-Kripke algorithm is implemented by the following formula:

$$D=P(W_{-4}A_{-4}+W_{-3}A_{-3}+W_{-2}A_{-2}+W_{-1}A_{-1}+ W_0A_0+W_{+1}A_{+1}+W_{+2}A_{+2})$$

where, D is a sleep condition value, $W_0$ is a weight of a current epoch (epoch 0), $A_0$ is a motion value of the current epoch (epoch 0), $W_{-1}$ is a weight of a previous epoch (epoch −1), $A_{-1}$ is a motion value of the previous epoch (epoch −1), $W_{+1}$ is a weight of a next epoch (epoch +1), $A_{+1}$ is a motion value of the next epoch (epoch +1), and so on. P is a scaling factor, and is adjusted to improve determining accuracy of the formula. When D is less than 1, it indicates that the current epoch (epoch 0) is in the sleep period. When D is greater than or equal to 1, it indicates that the current epoch (epoch 0) is in the awake period.

When this formula is applied to each epoch within the time period, the epochs are distinguished into the awake period and the sleep period within the time period.

In the foregoing embodiment, the Cole-Kripke algorithm is used to distinguish the epochs into the awake period and the sleep period within the time period. Other algorithms such as a Sadeh algorithm and a UCSD algorithm that are used to determine whether the user is in an active state or a rest state are also applicable to the disclosure.

Next, as described in step S150, each of the motion values corresponding to the at least one sleep period is transformed into a score according to a predetermined rule. The score represents activity intensity of the user in a corresponding epoch.

In an embodiment, the predetermined rule used in step S150 includes: when the motion value is less than a first value, the score is a positive value; when the motion value is greater than or equal to the first value but less than a second value, the score is a first negative value; and when the motion value is greater than or equal to the second value, the score is a second negative value, where the second negative value is less than the first negative value. A positive score represents that the user is calm without much motion. A more negative score represents that the user is more active. In an embodiment, for the convenience of calculation, the scores are all integers.

Details of the predetermined rule are adjusted according to an actual state. Table I below shows a specific example of the predetermined rule of the disclosure. G in the table represents a motion value.

TABLE I

| Predetermined rule | Score |
|---|---|
| G < 40 | 1 |
| 40 ≤ G < 50 | −2 |
| 50 ≤ G < 80 | −3 |
| 80 ≤ G < 200 | −5 |
| 200 ≤ G < 400 | −10 |
| 400 ≤ G < 600 | −20 |

In the predetermined rule shown in the table above, a total of six scores are set. Only one score is positive, all other scores are negative, and an absolute value of each negative score is greater than an absolute value of the positive score. The magnitude of the absolute value of each negative score approximately corresponds to the magnitude of the motion value.

Then, as described in step S160, a plurality of sleep depth scores is generated by using the scores, and the at least one sleep period is distinguished into at least one light sleep period and at least one deep sleep period by using the sleep depth scores.

In an embodiment, in step S160, the sleep depth score corresponding to each epoch is calculated by acuminating the scores before the epoch from the beginning of the sleep period. That is, the sleep depth score corresponding to each epoch is generated by summing up the score of the epoch and the score within the sleep period before the epoch. A positive or zero sleep depth score represents the deep sleep period, and a negative sleep depth score represents the light sleep period.

An example is taken together with the predetermined rule shown in Table I. Assuming that the motion value of the current epoch is 20, after the sleep period is entered, there are four epochs before the current epoch, whose motion values are 20, 30, 150, and 30 respectively. The sleep depth score calculated in this way is 1+1+(−5)+1+1=−1, which is determined as the light sleep period. Also, assuming that the motion value of the next epoch is 20, the sleep depth score corresponding to the next epoch calculated in this way is 1+1+(−5)+1+1+1=0, which is determined as the deep sleep period.

In the foregoing embodiment, after the sleep period is entered, the scores of all epochs before the current epoch are accumulated to calculate the sleep depth score. In other embodiments, a preset epoch quantity is alternatively set. After the sleep period is entered, before the current epoch, the scores of the epochs whose quantity is the preset epoch quantity are accumulated to calculate the sleep depth score. In an embodiment, when the preset epoch quantity is 5, the scores of the current epoch and five previous epochs of the current epoch are accumulated to determine whether the current epoch belongs to the deep sleep period or the light sleep period.

Next, in the foregoing embodiment, the score is accumulated from zero. In other embodiments, an initial score such as a negative integer is alternatively set, and the score is accumulated from the initial score, to avoid considering a case that the user calms down in a short time after the sleep period starts as the deep sleep period. This initial score is adjusted to improve accuracy of determining the light sleep period and the deep sleep period.

Then, as described in step S170, the heart rate values corresponding to the at least one deep sleep period are grouped as a high heart rate group and a low heart rate group by using an unsupervised learning algorithm.

In an embodiment, in step S170, a K-means clustering algorithm is used to group the heart rate values. The unsupervised learning method directly uses a heart rate value collected by the wearable electronic device for analysis without human intervention. Other algorithms used for grouping are also applicable to the disclosure.

FIG. 2 is a bar chart showing an embodiment of a result of grouping heart rate values by using a K-means clustering algorithm. In the figure, the horizontal axis is heart rate per second, and the vertical axis is count. The data on the right part is a high heart rate group, and an epoch corresponding to the high heart rate group is determined as a rapid eye movement period. The data on the left part is a low heart rate group, and an epoch corresponding to the low heart rate group is determined as a non-rapid eye movement period.

Next, as described in step S190, when the motion values corresponding to the high heart rate group satisfy a condition, it is determined that a behavior disorder event during rapid eye movement sleep happens.

In an embodiment, the condition is a threshold. In step S190, it is determined whether the motion values corresponding to the high heart rate group are greater than the threshold, and if so, it is determined that the behavior disorder event during rapid eye movement sleep happens to the user. The magnitude of the threshold is estimated by statistics.

In an embodiment, motion values of a group of normal people and a group of patients with a cerebral neurological disease (in an embodiment, Parkinson's disease) are analyzed. The Parkinson's disease patient is prone to the behavior disorder event during rapid eye movement sleep, so a value that causes a significant difference between the two groups is found as the threshold in step S190.

Figure 3:
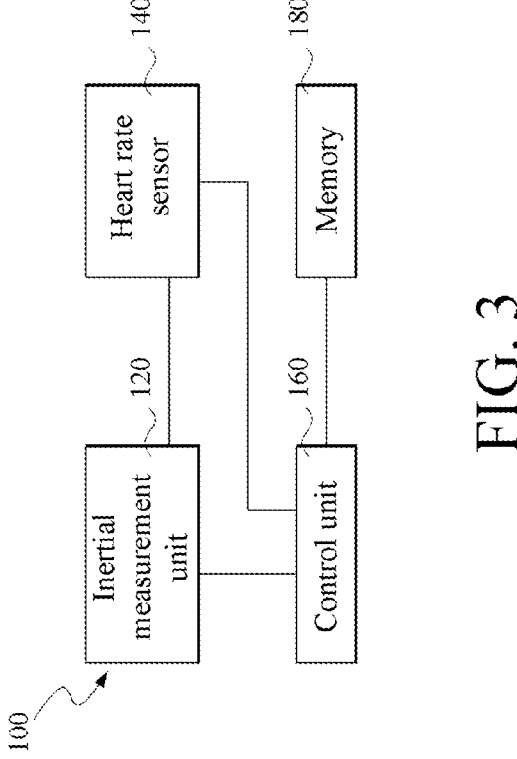
FIG. 3 shows an embodiment of a detecting system for a behavior disorder event during rapid eye movement sleep according to an embodiment of the disclosure.

FIG. 3 shows an embodiment of a detecting system 100 for a behavior disorder event during rapid eye movement sleep according to an embodiment of the disclosure. The detecting system 100 is arranged in a wearable electronic device. In other embodiments, the detecting system 100 is alternatively implemented by a wearable electronic device and a server in cooperation.

As shown in the figure, the detecting system 100 includes an inertial measurement unit 120, a heart rate sensor 140, a control unit 160, and a memory 180.

The control unit 160 is electrically connected to the inertial measurement unit 120 and the heart rate sensor 140, collects a heart rate value and a motion value of a user per epoch within a time period, and stores the values in the memory 180.

The control unit 160 uses the collected heart rate value and motion value for analysis in the collection process, or uses the collected heart rate value and motion value for analysis after the data collection is completed.

Also, in other embodiments, the control unit 160 alternatively only undertakes a data collection task, and transmits the collected heart rate value and motion value to another analysis device (in an embodiment, a server) for subsequent analysis processing.

In an embodiment, the control unit 160 stores the collected data together with an analysis result in the memory 180. In an embodiment, the control unit 160 performs personalized sleep analysis by using an unsupervised machine learning method, to detect a behavior disorder event during rapid eye movement sleep. In an embodiment, the control unit 160 de-identifies the collected data, and transmits the data to another analysis device for subsequent analysis processing.

The analysis device adjusts relevant parameters of the detecting method for a behavior disorder event during rapid eye movement sleep of the disclosure through machine learning, to improve the determining accuracy. The control unit 160 is a central processing unit or another electronic component with function of data collection and processing.

Figure 4:
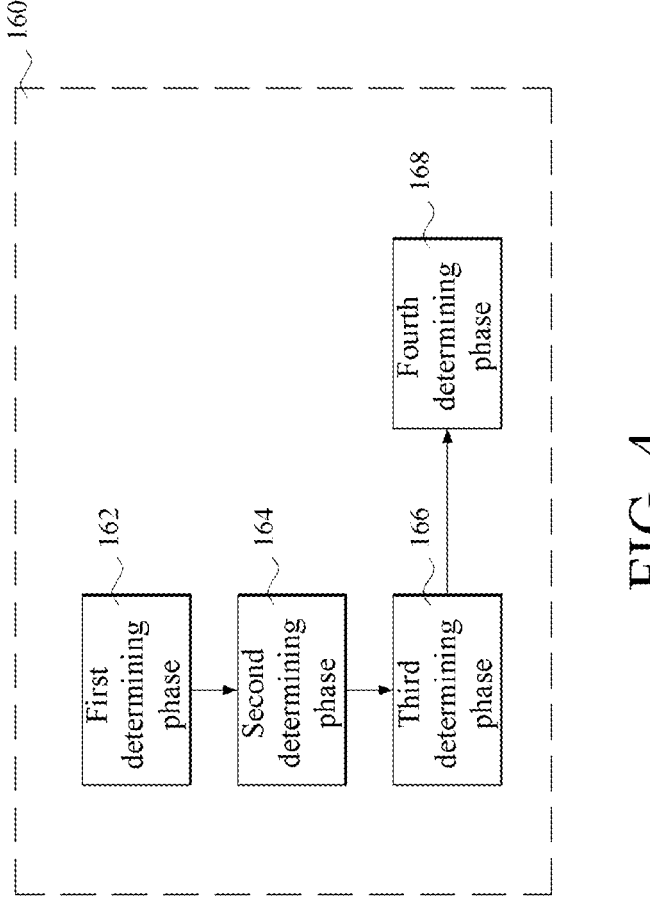
FIG. 4 shows an embodiment of a determining architecture executed by a control unit in FIG. 3.

FIG. 4 shows an embodiment of a determining architecture executed by a control unit 160 in FIG. 3.

The determining architecture is distinguished into a first determining phase 162, a second determining phase 164, a third determining phase 166, and a fourth determining phase 168. The first determining phase 162 distinguishes epochs into an awake period and a sleep period within a time period by using a collected motion value, that is, corresponds to step S130 in FIG. 1.

The second determining phase 164 analyzes an epoch determined as the sleep period. The second determining phase 164 transforms the motion value into a score according to a predetermined rule, and generates a plurality of sleep depth scores corresponding to each epoch within the sleep period by using the scores, to distinguish the sleep period into a light sleep period and a deep sleep period. The second determining phase 164 corresponds to steps S150 and S160 in FIG. 1.

The third determining phase 166 analyzes an epoch determined as the deep sleep period. The third determining phase 166 groups heart rate values as a high heart rate group and a low heart rate group, and determines an epoch that is determined as the deep sleep period and belongs to the high heart rate group as a rapid eye movement period. The third determining phase 166 corresponds to step S170 in FIG. 1.

The fourth determining phase 168 analyzes the epoch determined as the rapid eye movement period. The fourth determining phase 168 determines according to a corresponding motion value whether a behavior disorder event during rapid eye movement sleep happens. The fourth determining phase 168 corresponds to step S190 in FIG. 1.

In an embodiment, each of the foregoing determining phases is defined by a software program or firmware, and executed by the control unit 160.

The disclosure provides a simple and convenient detecting method and detecting system 100, to quickly determine whether the behavior disorder event during rapid eye movement sleep happens to the user. The detecting method and detecting system 100 are used matching a wearable electronic device, to effectively collect heart rate data and motion data of the user, thereby overcoming the conventional difficulty in detecting the behavior disorder event during rapid eye movement sleep.

The above is merely exemplary embodiments of the disclosure, and does not constitute any limitation on the disclosure. Any form of equivalent replacements or modifications to the technical means and technical content disclosed in the disclosure made by a person skilled in the art without departing from the scope of the technical means of the disclosure still fall within the content of the technical means of the disclosure and the protection scope of the disclosure.

What is claimed is:

1. A detecting method for a behavior disorder event during rapid eye movement sleep, applied to a wearable electronic device having an inertial measurement unit, a heart rate sensor, a control unit, and a memory, wherein the wearable electronic device is implemented with an unsupervised learning algorithm, and the detecting method comprising:

using the inertial measurement unit and the heart rate sensor to collect a heart rate value and a motion value of a user per epoch within a time period, and storing the heart rate values and the motion values in the memory;

after data collection is completed, causing the control unit to generate a plurality of corresponding sleep condition values by using the motion values, and distinguish the epochs into at least one awake period and at least one sleep period within the time period according to the sleep condition values, wherein each of the sleep condition values is generated by using at least two consecutive motion values;

when the at least one sleep period exists in the time period, causing the control unit to transform each of the motion values corresponding to the at least one sleep period into a score according to a predetermined rule, generate a plurality of sleep depth scores by using the scores, and distinguish the at least one sleep period into at least one light sleep period and at least one deep sleep period by using the sleep depth scores;

when the at least one deep sleep period exists in the at least one sleep period, causing the control unit to group the heart rate values corresponding to the at least one deep sleep period as a high heart rate group and a low heart rate group by using the unsupervised learning algorithm; and causing the control unit to determine, when the motion values corresponding to the high heart rate group satisfy a condition, an analysis result that a behavior disorder event during rapid eye movement sleep happens and store the analysis result in the memory;

wherein the unsupervised learning algorithm is K-means clustering algorithm;

wherein the step of generating the sleep depth scores by using the scores comprises: accumulating the scores before each epoch to generate the sleep depth scores;

wherein the control unit has a determining architecture including a first determining phase, a second determining phase, a third determining phase, and a fourth determining phase in a serial, wherein the first determining phase is for distinguishing epochs into the awake period and the sleep period, the second determining phase is for analyzing the epoch determined as the sleep period, the third determining phase is for analyzing the epoch determined as the deep sleep period, and the fourth determining phase is for analyzing the epoch determined as the rapid eye movement period.

2. The detecting method according to claim 1, wherein the epochs are distinguished into the at least one awake period and the at least one sleep period within the time period by using a Cole-Kripke algorithm.

3. The detecting method according to claim 1, wherein the predetermined rule comprises:

when the motion value is less than a first value, the score is a positive value;

when the motion value is greater than or equal to the first value but less than a second value, the score is a first negative value; and when the motion value is greater than or equal to the second value, the score is a second negative value, wherein the second negative value is less than the first negative value.

4. The detecting method according to claim 1, wherein the step of generating the sleep depth scores by using the scores comprises:

accumulating the scores before each epoch to generate the sleep depth scores.

5. The detecting method according to claim 1, wherein the step of generating the sleep depth scores by using the scores comprises:

setting an initial score; and accumulating the scores before each epoch from the initial score, to generate the sleep depth scores.

6. The detecting method according to claim 1, wherein the motion value is an inertial measurement value.

7. The detecting method according to claim 6, wherein the inertial measurement value comprises an X-direction acceleration measurement value, a Y-direction acceleration measurement value, and a Z-direction acceleration measurement value.

8. The detecting method according to claim 1, wherein the condition is that at least one of the motion values corresponding to the high heart rate group is greater than a threshold.

9. The detecting method according to claim 1, wherein the heart rate value is an R-wave-to-R-wave interval (RR interval) value of an electrocardiogram signal.

10. The detecting method according to claim 1, wherein a duration of the epoch is 30 seconds.

11. A detecting system for a behavior disorder event during rapid eye movement sleep, comprising:

an inertial measurement unit;

a heart rate sensor;

a memory; and a control unit, electrically connected to the inertial measurement unit and the heart rate sensor, wherein a heart rate value and a motion value of a user per epoch within a time period are collected through the inertial measurement unit and the heart rate sensor, and are stored in the memory; and the control unit is configured to execute a determining architecture, wherein the determining architecture comprises:

a first determining phase defined by a first program code, which is executed to distinguish the epochs into at least one awake period and at least one sleep period within the time period according to the sleep condition values, wherein each of the sleep condition values is generated by using at least two consecutive motion values;

a second determining phase defined by a second program code, which is executed to transform each of the motion values corresponding to the at least one sleep period into a score according to a predetermined rule, generate a plurality of sleep depth scores by using the scores, and distinguish the at least one sleep period into at least one light sleep period and at least one deep sleep period by using the sleep depth scores, wherein the sleep depth scores are generated by accumulating the scores before each epoch;

a third determining phase defined by a third program code, which is executed to group the heart rate values corresponding to the at least one deep sleep period as a high heart rate group and a low heart rate group by using an unsupervised learning algorithm; and a fourth determining phase defined by a fourth program code, which is executed to determine, when the motion values corresponding to the high heart rate group satisfy a condition, that a behavior disorder event during rapid eye movement sleep happens;

wherein the unsupervised learning algorithm is K-means clustering algorithm;

wherein the control unit has a determining architecture including the first determining phase, the second determining phase, the third determining phase, and the fourth determining phase in a serial, wherein the first determining phase is for distinguishing epochs into the awake period and the sleep period, the second determining phase is for analyzing the epoch determined as the sleep period, the third determining phase is for analyzing the epoch determined as the deep sleep period, and the fourth determining phase is for analyzing the epoch determined as the rapid eye movement period.

12. A detecting method for a behavior disorder event during rapid eye movement sleep, applied to a wearable electronic device having an inertial measurement unit, a heart rate sensor, a control unit, and a memory, wherein the wearable electronic device is implemented with an unsupervised learning algorithm, and the detecting method comprising:

using the inertial measurement unit and the heart rate sensor to collect a heart rate value and a motion value of a user per epoch within a time period, and storing the heart rate values and the motion values in the memory;

after data collection is completed, causing the control unit to generate a plurality of corresponding sleep condition values by using the motion values, and distinguish the epochs into at least one awake period and at least one sleep period within the time period according to the sleep condition values, wherein each of the sleep condition values is generated by using at least two consecutive motion values;

when the at least one sleep period exists in the time period, causing the control unit to transform each of the motion values corresponding to the at least one sleep period into a score according to a predetermined rule, generate a plurality of sleep depth scores by using the scores, and distinguish the at least one sleep period into at least one light sleep period and at least one deep sleep period by using the sleep depth scores;

when the at least one deep sleep period exists in the at least one sleep period, causing the control unit to group the heart rate values corresponding to the at least one deep sleep period as a high heart rate group and a low heart rate group by using the unsupervised learning algorithm; and causing the control unit to determine, when the motion values corresponding to the high heart rate group satisfy a condition, an analysis result that a behavior disorder event during rapid eye movement sleep happens and store the analysis result in the memory;

wherein the unsupervised learning algorithm is K-means clustering algorithm;

wherein the predetermined rule comprises:

when the motion value is less than a first value, the score is a positive value;

when the motion value is greater than or equal to the first value but less than a second value, the score is a first negative value; and when the motion value is greater than or equal to the second value, the score is a second negative value, wherein the second negative value is less than the first negative value;

wherein the control unit has a determining architecture including a first determining phase, a second determining phase, a third determining phase, and a fourth determining phase in a serial, wherein the first determining phase is for distinguishing epochs into the awake period and the sleep period, the second determining phase is for analyzing the epoch determined as the sleep period, the third determining phase is for analyzing the epoch determined as the deep sleep period, and the fourth determining phase is for analyzing the epoch determined as the rapid eye movement period.

* * * * *